United States Patent
Flohr et al.

(10) Patent No.: US 9,993,216 B2
(45) Date of Patent: Jun. 12, 2018

(54) CREATING A RESULTANT IMAGE FOR A SPECIFIABLE, VIRTUAL X-RAY QUANTA ENERGY DISTRIBUTION

(71) Applicants: Thomas Flohr, Uehlfeld (DE); Steffen Kappler, Effeltrich (DE); Rainer Raupach, Heroldsbach (DE); Bernhard Schmidt, Fürth (DE)

(72) Inventors: Thomas Flohr, Uehlfeld (DE); Steffen Kappler, Effeltrich (DE); Rainer Raupach, Heroldsbach (DE); Bernhard Schmidt, Fürth (DE)

(73) Assignee: Siemens Aktiengesellschaft, München (DE)

( * ) Notice: Subject to any disclaimer, the term of this patent is extended or adjusted under 35 U.S.C. 154(b) by 71 days.

(21) Appl. No.: 15/068,554

(22) Filed: Mar. 12, 2016

(65) Prior Publication Data
US 2016/0262713 A1 Sep. 15, 2016

(30) Foreign Application Priority Data
Mar. 12, 2015 (DE) .......................... 10 2015 204 450

(51) Int. Cl.
*A61B 6/03* (2006.01)
*A61B 5/00* (2006.01)
*A61B 6/00* (2006.01)

(52) U.S. Cl.
CPC ............ *A61B 6/5205* (2013.01); *A61B 6/032* (2013.01); *A61B 6/482* (2013.01); *A61B 5/0077* (2013.01)

(58) Field of Classification Search
CPC ....... A61B 5/0077; A61B 6/032; A61B 6/482; A61B 6/5205
See application file for complete search history.

(56) References Cited

U.S. PATENT DOCUMENTS

2010/0014737 A1* 1/2010 Ruhrnschopf ......... A61B 6/032
                                                  382/131
2011/0280458 A1 11/2011 Flohr et al.
(Continued)

FOREIGN PATENT DOCUMENTS

DE 102008030552 A1 * 12/2009 ............. A61B 6/032
DE 102008030552 A1 12/2009
(Continued)

OTHER PUBLICATIONS

German Office action for related German Application No. 10 2015 204 450.5, dated Oct. 30, 2015 with English Translation.

*Primary Examiner* — Mark R Gaworecki
(74) *Attorney, Agent, or Firm* — Lempia Summerfield Katz LLC

(57) ABSTRACT

A method for creating a resultant image for a specifiable, virtual x-ray quanta energy distribution includes capturing a first image dataset of the patient, capturing at least one second image dataset of the patient, and specifying a virtual x-ray quanta energy distribution. The method also includes establishing a spatial density distribution of the patient for at least two materials based on the first image dataset and the at least one second image dataset. The method includes creating a third image dataset of the patient based on the specified virtual x-ray quanta energy distribution and the established spatial material density distributions. The third image dataset represents an x-ray attenuation distribution of the patient corresponding to the specified virtual x-ray quanta energy distribution. The method also includes creating the virtual image from the third image dataset.

22 Claims, 2 Drawing Sheets

(56) References Cited

U.S. PATENT DOCUMENTS

2014/0037045 A1 2/2014 Dafni et al.
2014/0112441 A1 4/2014 Becker et al.

FOREIGN PATENT DOCUMENTS

DE 102010020770 A1 11/2011
DE 102012219051 A1 4/2014

* cited by examiner

CREATING A RESULTANT IMAGE FOR A SPECIFIABLE, VIRTUAL X-RAY QUANTA ENERGY DISTRIBUTION

This application claims the benefit of DE 10 2015 204 450.5, filed on Mar. 12, 2015, which is hereby incorporated by reference in its entirety.

BACKGROUND

The present embodiments relate to creating a resultant image based on at least two image data records.

Ever more frequent use is being made of imaging x-ray devices (e.g., a C-arm x-ray device or a computed tomography device) for the resolution of medical issues. What imaging x-ray devices have in common is that imaging x-ray devices have an x-ray source (e.g., an x-ray tube), as well as an x-ray detector interacting with the x-ray source. The x-ray radiation emitted by the x-ray source passes through a patient to be examined and is attenuated by interacting with the different tissue types of the patient. The detector is disposed beyond the patient in relation to the x-ray source, accepts the remaining x-ray radiation beyond the patient, and converts the x-ray radiation into the electrical signals corresponding to the x-ray attenuation caused by the patient.

The x-ray source emits x-ray radiation with one emission spectrum, which provides that the gamma quanta emitted by the x-ray source have an energy distribution including a plurality of quanta energy values. In other words, the x-ray source emits polychromatic x-ray radiation. The emission spectrum is decisively influenced by the x-ray tube voltage or the acceleration voltage with which the x-ray source is operated. In general terms, the higher the acceleration voltage is, the greater the average x-ray quanta energy of the emission spectrum also is.

It is known that different materials or tissue types (e.g., water or bones) interact with x-ray radiation to different degrees. Expressed in simpler terms, the image contrast in all x-ray images is based on these differences. The energy dependence of the x-ray attenuation on passage through material is also known. This provides that low-energy x-ray radiation is absorbed more strongly by material than higher-energy x-ray radiation.

These differences in the interaction between x-ray radiation and material is to be taken into account during x-ray imaging in order to create x-ray images that have sufficient image quality to respond to the medical issue and protect the patient from an unnecessary dose load.

The acceleration voltage may be set for this purpose before an x-ray image is recorded. The decisive factors in the choice of a suitable acceleration voltage are the underlying medical issue, the image quality to be achieved, a reduction of the patient dose, or the amount of contrast medium to be administered for the x-ray and/or individual x-ray attenuation characteristics of a patient. Thus, low acceleration voltages ranging from 70 kV to 100 kV may be used for the x-ray image recording while administering contrast media containing iodine in order to optimize the iodine contrast-to-noise ratio with a low dose, while higher acceleration voltages, such as around 140 kV, are then employed, for example, if instead there are likely to be strong metal artifacts in the x-ray images.

Until now, the user (e.g., a doctor or a medical specialist) has set the acceleration voltage manually. For this purpose, modern x-ray imaging devices have automatic dosing systems available to them, with the aid of which the acceleration voltage is set automatically or semi-automatically for an x-ray scan or an x-ray image. In such cases, the automatic dosing system offers the user a choice of acceleration voltages in the definition of the scan protocol (e.g., 70 kV, 80 kV, 100 kV, 120 kV and 140 kV), from which a selection of the optimum acceleration voltage is made as a function of the planned examination, the anatomical circumstances of the patient, the image quality, and/or characteristics of the x-ray imaging device. As an alternative, the automatic dosing system just shows the user a corresponding suggestion for the optimum acceleration voltage for confirmation or sets the optimum acceleration voltage automatically.

Accordingly, imaging x-ray devices have previously had to be embodied such that the imaging x-ray devices are able to be operated with a number of different acceleration voltages. In other words, the ability to set the acceleration voltage on the part of the generator and also the x-ray source is to be provided, the x-ray tube voltage is to be able to be adapted to the optimum acceleration voltage with a constant output, and the different acceleration voltages are to be calibrated, which provides a greater technical outlay. The setting of the x-ray tube voltage on the part of the user is complex and thereby prone to errors.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a user is provided with x-ray images that, with respect to an image impression, image quality, and/or meaningfullness, are comparable with x-ray images that would have been obtained by an x-ray scan with the optimum acceleration voltage, while dispensing with complex selection or definition of an optimum acceleration voltage or while dispensing with a need to provide an x-ray imaging device able to be set to all possible acceleration voltages.

Features, advantages or alternate forms of embodiment mentioned here are likewise also to be transferred to the other subject matter and vice versa. In other words, the claims (e.g., directed to a device) may also be further developed with the features that are described or claimed in conjunction with a method. The corresponding functional claims of the method embodied in such cases by corresponding physical modules of the method are embodied in such cases by corresponding physical modules or units.

One or more of the present embodiments are based on the capture of a first image dataset of a patient representing a first x-ray attenuation distribution of the patient in accordance with a first x-ray quanta energy distribution, and the capture of at least one second image dataset of the patient representing at least one second x-ray attenuation distribution of the patient in accordance with a second x-ray quanta energy distribution. A virtual x-ray quanta energy distribution is specified. Based on the first and the at least one second image dataset, a spatial density distribution in the patient for at least two materials may be established, and from this, as well as on the basis of the specifiable, virtual x-ray quanta energy distribution, a third image dataset of the patient may be created. The third image dataset represents a third x-ray attenuation distribution of the patient corresponding to the specifiable, virtual x-ray quanta energy distribution. A resultant image is created from this third dataset.

In a method, at least two x-ray image datasets with x-ray quanta energy distributions differing from one another are created from the patient. The image datasets may be captured with an embodiment of an x-ray imaging device, which will be explained in greater detail below. The image datasets may involve a part area of the body of the patient (e.g., a specific region of the patient's body that is to be imaged) using an x-ray imaging device. In this case, the image datasets contain information about the x-ray attenuation distribution of the patient relating only to the part area to be imaged (e.g., in relation to the thorax or the pelvis). As an alternative, the image datasets involve the entire body of the patient. In this case, the image datasets contain information about the x-ray attenuation distribution of the patient in relation to the patient's entire body.

An x-ray quanta energy distribution refers to the energetic spectrum of the x-ray radiation that was used to record one of the image datasets. The at least two image datasets are created with x-ray radiation that has x-ray quanta energy distributions deviating from one another. The x-ray quanta energy distributions may differ, for example, in average x-ray quanta energy or in peak energy, or the x-ray quanta energy distributions may partly overlap spectrally or be entirely separated (e.g., not have any intersection).

The at least two image datasets may be created with a dual or a multi-energy x-ray imaging device. The different x-ray quanta energy distributions in such cases are created by different acceleration voltages at the corresponding x-ray source or sources of the x-ray imaging device used. As an alternative, the different x-ray quanta energy distributions may be created with different spectral filters beyond the x-ray source, and/or energy-selective detectors may be used. Energy-selective may be spectrally-resolving or spectrally-separating. Energy-selective detectors are configured to classify incident x-ray quanta in accordance with respective quantum energy.

The x-ray quanta energy distributions used for recording the image datasets are any given distributions and may be specified or fixed in advance by the x-ray imaging device used and by one or more corresponding acceleration voltages or other system parameters. The x-ray quanta energy distributions deviate from the x-ray quanta energy distribution actually desired by the user for the x-ray scan.

A specifiable, virtual x-ray quanta energy distribution may be a further x-ray radiation spectrum that differs from the first and the second x-ray quanta energy distribution. This x-ray quanta energy distribution is able to be specified in the sense that the x-ray quanta energy distribution may be selected, defined, or determined by a computer system of the x-ray imaging device, as is described below, or may be entered by a user. This x-ray quanta energy distribution is virtual, because, by contrast with the first and at least one second x-ray quanta energy distributions, no image dataset is created with the x-ray quanta energy distribution by measurement. A third image dataset is computed from the at least two image datasets. In other words, for the third x-ray quanta energy distribution, the recording of an image dataset is simulated. The specifiable, virtual x-ray quanta energy distribution corresponds to the x-ray quanta energy distribution actually desired by the user for the x-ray scan.

In accordance with one or more of the present embodiments, the specifiable, virtual x-ray quanta energy distribution is only given by one energy value. In this case, the resultant image reconstructed from the third image dataset involves a monochromatic image. For example, the specifiable, virtual x-ray quanta energy may be the average energy of an emission spectrum of an x-ray source with which an x-ray image corresponding to the resultant image would have been created. In accordance with another form of embodiment, the specifiable, virtual x-ray quanta energy distribution is given by a narrow energy band (e.g., an energy band of 5 keV, 10 keV, 15 keV or the like), and the resultant image corresponds to a polychromatic image. In accordance with a further form of embodiment, the specifiable, virtual x-ray quanta energy distribution lies between the first and the at least one second x-ray quanta energy distribution. For example, the specifiable, virtual x-ray quanta energy distribution in this case does not exhibit any overlapping with one of the other x-ray quanta energy distributions.

The x-ray attenuation is an energy-dependent variable. Thus, the first image dataset represents the x-ray attenuation distribution of the patient for the first x-ray energy spectrum, and the at least one second image dataset represents the x-ray attenuation distribution of the patient for the at least one second x-ray energy spectrum.

One or more of the present embodiments use this differing information about the x-ray attenuation distribution in the at least two image datasets in order to create a resultant image for the specifiable, virtual x-ray quanta energy distribution.

To do this, a material or basic material decomposition known per se of the at least two image datasets into at least two materials is carried out. The material decomposition is based on the consideration that an x-ray attenuation value measured by an x-ray imaging device may be described as a linear combination of x-ray attenuation values of basic materials in relation to the x-ray quanta energy distribution. Measured x-ray attenuation values are produced from the at least two image datasets for different x-ray quanta energy distributions. Material or basic material may be any substance or any given tissue (e.g., water), contrast media such as iodine, soft tissue, bones and the like. The x-ray attenuation of a basic material as a function of the energy of the x-ray radiation is basically known or may be determined by prior measurements on phantoms and may be stored in the form of tables for retrieval within the framework of material decomposition. The result of the material decomposition is a spatial density distribution of the at least two materials in the patient, from which, for each volume element in the region of the body to be imaged, the basic material portions or the basic material combination are able to be established. On the basis of the known, energy-dependent x-ray attenuation of the two materials, by addition of the x-ray attenuation values of the two materials weighted according to the material portion, a third image dataset is calculated or simulated for the specifiable, virtual x-ray quanta energy distribution. This describes an effective x-ray attenuation that would have been produced by an x-ray image with the specifiable, virtual x-ray quanta energy distribution and subsequent image reconstruction. In accordance with a form of embodiment, there may also be an energy-dependent weighting in the addition of the x-ray attenuation portions for the specifiable, virtual x-ray quanta energy distribution. In accordance with one form of embodiment, the third image dataset is composed of a plurality of individual image datasets for discrete x-ray quanta energy values within the specifiable, virtual x-ray quanta energy distribution.

The resultant image subsequently reconstructed from the third image dataset using known reconstruction algorithms (e.g., a filtered back projection or an iterative algorithm) gives the impression of having been recorded with x-ray radiation of the specifiable, virtual x-ray quanta energy distribution, without the user having to select an acceleration voltage for the x-ray source corresponding to one of the x-ray quanta energy distributions beforehand.

The method of operation provides that the necessity of setting the x-ray quanta energy distribution via the choice of the acceleration voltage of an x-ray source according to the desired image impression before the recording of the image datasets with an x-ray imaging device is dispensed with. This makes a simplified structure of the x-ray imaging device possible and slims down the previously complex and error-prone operating process for the user.

In accordance with a first aspect, the capturing of the first and of the at least one second image dataset is done with a spectrally-separating x-ray radiation detector. This is configured to classify incident x-ray quanta in accordance with quantum energy and assign the incident x-ray quanta to one of the image datasets in each case. In this way, only one x-ray source with a specified or fixed emission spectrum may be provided for the method. In accordance with this aspect, the image datasets are recorded especially quickly and without additional dose load for the patient.

In accordance with a further aspect, the first and the at least one second image dataset are captured with a quanta-counting detector or with a two-layer detector.

A quanta-counting detector may be a direct converting detector that converts an incident x-ray quantum using suitable detector material directly into an electrical signal. Quanta-counting detectors may be operated in energy-resolving mode. The energy resolution is able to be set by binning. In other words, any given energy ranges may be defined, in relation to which incident x-ray quanta may be classified. The first and the at least one second image dataset are each formed by signals within one or more energy ranges. The energy ranges may be assigned to the image datasets as a function of the first and/or at least one second x-ray quanta energy distribution or as a function of the specifiable, virtual x-ray quanta energy distribution. The semiconductors cadmium-telluride, cadmium-zinc-telluride or gallium-arsenide or, in the case of a flat-panel detector, amorphous selenium or the like are suitable as detector materials for quanta-counting detectors.

A two-layer detector or also dual or double-layer detector is embodied to break down the incident x-ray tube spectrum into a low-energy and a high-energy portion. The double-layer detector is constructed from two layers. A detector layer facing towards the x-ray source measures photons of the incident x-ray radiation with low energy and allocates the measured signals to the first image dataset. High-energy x-ray radiation passes through the detector. Photons with higher quantum energy are measured in the detector layer disposed below or beyond (e.g., by the detector layer facing away from the x-ray source and assigned to the second image dataset). Typically, both detector layers include a scintillator, and consequently, the double-layer detector involves an indirect-converting detector. Crystals such as cesium iodide, cadmium tungstate or ceramic substances (e.g., gadolinium oxysulfide or the like) are used as scintillation material.

This aspect allows an adaptation of detector parameters in a simple way (e.g., by adapting the binning to the specifiable, virtual x-ray quanta energy distribution). Though this, the information relating to the x-ray attenuation distribution of the patient in the image datasets becomes especially valuable.

If a double-layer detector is used in the method, it is advantageous to operate the x-ray source with an acceleration voltage of 120 kV defined beforehand. If a quanta-counting detector is used, it is advantageous to operate the x-ray source with an acceleration voltage of 140 kV defined beforehand. In this way, account is taken of the physical characteristics (e.g., the energy-dependent sensitivity) of the respective detector.

In accordance with a further embodiment, the at least two image datasets are captured with two source detector systems that work with different emission spectra. In this case, the x-ray module of the x-ray imaging device includes two x-ray sources, and the detector module includes two x-ray radiation detectors. Each detector is configured for recording the x-ray radiation emanating from one of the x-ray sources. Such a device is also referred to as a dual-source x-ray imaging device. In accordance with a further embodiment, the two x-ray sources are operated with the acceleration voltages of 90 kV and 150 kV during capturing of the at least two image datasets. In accordance with a further embodiment, at least one of the two x-ray sources includes a filter for improving the spectral separation of the x-ray radiation emanating from the source (e.g., a tin filter).

In accordance with a further aspect, the virtual x-ray quanta energy is specified as a function of at least one item of patient-specific, body-related information of the patient.

An item of patient-specific, body-related information may be any item of information for a patient that makes a statement about the individual morphology or anatomy of their body. For example, this may be the patient's height (e.g., extent from head to foot along a body axis), extent in the lateral direction (e.g., the width of the patient), extent in the anterior-posterior direction (e.g., depth of the patient), body surface, or the patient's weight. Other information about the body such as, for example, a particular tissue distribution, tissue composition, the location or size of specific organs or tissue in absolute terms or relative to one another, or the individual x-ray attenuation behavior, for example, are likewise included. The body surface of the patient may be the three-dimensional surface formed by the skin of the patient or clothing or covering or the like resting thereon, which delimits the patient from their environment. Patient weight may be the distribution of mass in accordance with the tissue density of the patient's body (e.g., the weight of the patient is to be understood by this).

This aspect is based on the consideration that an especially meaningful resultant image may be created if, during the specification of the virtual x-ray quanta energy distribution, anatomical circumstances of the patient that take account of the individual x-ray attenuation characteristics of the patient are considered. This method corresponds to selecting an acceleration voltage for an x-ray source as a function of patient-specific, body-related information. Accordingly, the specifiable, virtual x-ray quanta energy distribution is selected so that the distribution corresponds to the average energy of an emission spectrum, for example, that would have been suitable for the recording of an image dataset taking into consideration the anatomical circumstances of the patient.

At least one or more items of patient-specific, body-related information is produced by the evaluation of a patient topogram, a photographic image of the patient, or one or more x-ray images of the patient that stem from x-ray examinations lying in the past, for example. A topogram or a photographic recording represents the patient in at least the region of the body to be imaged or entirely. As an alternative, the x-ray imaging device may be configured to establish at least one item of patient-specific, body-related information about the patient (e.g., a set of scales may be integrated into the patient couch of the x-ray imaging device for determining the patient's weight, or the x-ray imaging device may include a camera for creating a photographic image of the patient. In a further embodiment, an entry of patient-specific, body-related information may be made by the user via in input unit not described in any greater detail below.

In accordance with a further aspect, the virtual x-ray quanta energy is specified based on the at least one of the following items of patient-specific, body-related information: Patient height, patient width, patient shape, patient weight, or x-ray attenuation behavior of the patient. The variables or information are well suited for meeting an appropriate choice for the specifiable, virtual x-ray quanta energy distribution for the patient. Patient height, patient width, patient shape and x-ray attenuation behavior may be derived, for example, by known image processing algorithms from a topogram and/or from a photographic image of the patient. The shape of the patient may be determined by a three-dimensional surface model for the body surface of the patient, at least in the region of the body to be imaged.

In accordance with a further aspect, the at least one item of patient-specific, body-related information may be obtained by optical scanning of the patient.

The patient is scanned by optical sensors. The optical sensor is configured to detect electromagnetic radiation that has been reflected and/or emitted by the patient. The optical sensor is further configured to detect electromagnetic radiation in a lower spectral range by comparison with x-ray radiation (e.g., in the visible or infrared spectral range). During scanning with the optical sensor, the patient is consequently not subjected to any potentially damaging, additional x-ray radiation, such as, for example, would be the case during the recording of a topogram with the x-ray imaging device for obtaining patient-specific, body-related information. The patient may be scanned directly before the x-ray image or the x-ray scan. However, this temporal relationship is not absolutely necessary. The patient may lie on his back during the scan and on the patient couch of the x-ray imaging device, so that the patient-specific, body-related information obtained thereby reproduces the anatomical circumstances during the x-ray image in the best-possible way. The optical sensor is embodied to create two-dimensional or three-dimensional information during the scan.

In accordance with a further aspect, the optical scanning is done by a three-dimensional camera.

In this case, the optical sensor, in the form of a three-dimensional camera, records three-dimensional information about the patient in at least the region of the body to be imaged. Accordingly, the optical sensor in accordance with this form of embodiment is configured for non-contact scanning of the surface of an object and, for example, the surface of the patient's body. The three-dimensional information contains depth information and may be present, for example, in the form of a three-dimensional image. In other words, the three-dimensional information, for each object point or for each pixel, contains additional information about the distance between the object and the sensor. By contrast with a two-dimensional image, which merely images an object in two dimensions with gray scale or color values, a three-dimensional image is valuable because of enhanced information content in relation to the at least one item of patient-specific, body-related information.

The optical scanning of the patient may be restricted to the body region to be scanned. This speeds up the establishment of the at least one item of patient-specific, body-related information. In one embodiment, the entire patient is scanned in order to be able to derive a number of items of patient-specific, body-related information especially precisely. By taking into consideration any given combination of patient-specific, body-related information, the specifiable, virtual x-ray quanta energy distribution may be adapted especially well to the anatomy of the patient.

In accordance with a further aspect, the virtual x-ray quanta energy is specified as a function of an examination type (e.g., the planned examination type that is to take place on the basis of the resultant image for the patient). Examination type in such cases may be any given medical or clinical issue that may be responded to based on x-ray images. For example, an examination of blood vessels by an angiography recording or an examination of the liver parenchyma may take place with administration of a contrast medium in each case, or an examination of bone tissue may take place without contrast medium.

This aspect is based on the consideration that the image quality of the resultant image may be optimized by the virtual x-ray quanta energy distribution being specified while taking into consideration the type of the examination, since each examination type imposes different demands on the x-ray image. This aspect thus essentially corresponds to the choice of a suitable acceleration voltage, which would have led to a desired image impression or an image impression necessary for responding to a clinical issue, were the recording of the image dataset to have taken place with this acceleration voltage. Through the choice of a suitable, specifiable, virtual x-ray quanta energy distribution, the recording of a image dataset for an acceleration voltage corresponding to one of the specifiable, virtual x-ray quanta energy distributions is simulated.

In accordance with a further aspect, the virtual x-ray quanta energy is specified as a function of a desired image quality (e.g., with respect to an improved contrast-to-noise ratio), reduced image noise, or reduced artifacts. Artifacts may be all phenomena contained in an x-ray image that do not correspond to anything in the physical size of an object to be imaged. Typical artifacts are, for example, metal artifacts, beam hardening artifacts, movement artifacts, part volume artifacts, and the like.

This aspect also essentially corresponds to the choice of a suitable acceleration voltage that would have led to a desired image impression or an image impression necessary for responding to a clinical issue, were the recording of the image dataset to have taken place with this acceleration voltage. Thus, for example, a small x-ray tube voltage is chosen for the image recording when an especially good iodine contrast is required, as in the case, for example, in the examination of blood vessels or soft tissue. Correspondingly, according to this aspect, the choice of the specifiable, virtual x-ray quanta energy distribution may be made accordingly for improving the iodine contrast in the range of smaller x-ray quanta energies (e.g., between 50 keV and 90 keV). In an alternate situation, the specifiable, virtual x-ray quanta energy distribution may be chosen in the range of higher x-ray quanta energies (e.g., as from 100 keV upwards) if it is known that metallic structures are included in the patient's body (e.g., joint implants or screws after a bone fracture, the artifacts of which are to be reduced in the resultant image).

In accordance with a further aspect, the virtual x-ray quanta energy is specified after capturing the at least two image datasets with the x-ray imaging device. One or more of the present embodiments allow the definition of the virtual x-ray quanta energy both before and also after the capturing of the at least two image datasets. In the event of a retrospective consideration, the virtual x-ray quanta energy distribution may, however, be specified as a function of information (e.g., patient-specific, body-related information or a desired examination type that was still unknown at the time of the capture). This allows a wide use of the present embodiments. Apart from this, the retrospective choice of the specifiable, virtual x-ray quanta energy distribution allows a number of resultant images to be simulated for different virtual x-ray quanta energy distributions and the optimum resultant image only to be selected retrospectively based on the image impression created in each case. In other words, in accordance with one or more of the present embodiments, at least one third image dataset may be created, and at least one resultant image may be reconstructed from this.

For the case of a prospective specification of the virtual x-ray quanta energy distribution, optimized scan parameters may also be derived from the virtual x-ray quanta energy distribution. For example, with a fixed specified acceleration voltage, the x-ray tube current may be adapted as well to reduce the overall dose, or the energy thresholds or the binning of the spectrally resolving detector may be adapted to the specifiable, virtual x-ray quanta energy distribution in order to create image datasets that contain an optimized information content with respect to the specifiable, virtual x-ray quanta energy distribution. There may be account taken prospectively of physical characteristics of the detector (e.g., the energy-dependent response characteristic or the signal separation behavior in the choice of the virtual x-ray quanta energy distribution).

In accordance with a further aspect, the virtual x-ray quanta energy is specified by a user. For this purpose, the x-ray imaging device has a suitable input unit (e.g., the input unit detects movement, touch and/or speech of the user and derives commands therefrom to define the specifiable, virtual x-ray quanta energy distributions). The user may, for example, directly enter a desired, virtual x-ray quanta energy distribution, but the user may also enter a desired acceleration voltage, which is converted or changed by the x-ray imaging device in accordance with a specification into a virtual x-ray quanta energy distribution. As an alternative and/or in addition, the user may also enter the examination type, or a desired contrast-to-noise ratio or a desired image noise. An entry by the user may be the x-ray imaging device displaying for the user, via a display or output device intended for the purpose, possible values for the virtual x-ray quanta energy distribution or corresponding acceleration voltage for selection. The same also applies for the examination type or the image quality. In this way, the user may be presented with a user interface that the user is used to. In this case, the process is referred to as a semi-automated specification of the virtual x-ray quanta energy. In addition, the virtual x-ray quanta energy distribution may be specified automatically by the x-ray imaging device. The x-ray imaging device may automatically take into consideration information relating to the desired image quality or the planned examination type. The specifications may be made by the user using the input unit or captured in another way by the x-ray imaging device or transmitted to the device.

In accordance with a further aspect, the basic materials are iodine and soft tissue. In this case, the at least two image datasets are captured while iodine contrast medium is administered. This type of x-ray image represents the predominant proportion of all x-ray images. Further examples are the decomposition into the materials or basic materials water and bone tissue for better presentation of bone portions, collagen, and soft tissue for better presentation of tendons and ligaments, and the like. There may be a decomposition into more than two basic materials (e.g., into bone mineral, red and yellow bone marrow). This decomposition is undertaken in accordance with the known method and is based on more than two captured image datasets. Each image dataset is able to be assigned an x-ray quanta energy distribution. These x-ray quanta energy spectra differ from one another. The more than two image datasets are created, for example, either with more than two different acceleration voltages of one or more x-ray sources and/or by spectral separation and/or by energy-resolving detectors from one or more detected x-ray quanta energy spectra.

The materials may be selected by the user or automatically by the x-ray imaging device. For the selection, information about the region of the body of the patient to be imaged or the planned examination type may be taken into consideration.

One or more of the present embodiments further relate to a computer program with program code for carrying out all method acts in accordance with one or more embodiments of the method when the program is executed in a computer. This provides that the method is able to be carried out reproducibly and with less susceptibility to errors on different computers.

One or more of the present embodiments also relate to a machine-readable data medium on which the computer program described above is stored.

One or more of the present embodiments relate to an x-ray imaging device for creating a resultant image of a patient for a specifiable, virtual x-ray quanta energy. The x-ray imaging device includes an x-ray module including at least one x-ray source for creating and emitting x-ray radiation in each case with a specifiable x-ray quanta energy distribution, a detector module including at least one x-ray radiation detector for detecting x-ray radiation emitted by the x-ray radiation module, and includes a computer system that carries out the acts of the method of one or more of the present embodiments during operation.

The x-ray imaging device includes an x-ray device that is configured for recording a plurality of x-ray projections from different projection angles (e.g., a computed tomography device with an annular rotating frame) or involves a C-arm x-ray device. The recordings may be created during a rotational movement (e.g., continuous) of a recording unit including an x-ray module and a detector module interacting with the x-ray source. An x-ray source include an x-ray tube with rotating anode. An x-ray radiation detector for a computed tomography device includes a row detector with a number of rows for example. An x-ray detector for a C-arm x-ray device includes a flat-panel detector, for example. The x-ray detector may be embodied as both an energy-resolving and also a counting detector.

One or more of the present embodiments further relate to an x-ray imaging device for creating a resultant image of a patient for a specifiable, virtual x-ray quanta energy distribution. The x-ray imaging device includes an x-ray module including at least one x-ray source for creating and emitting x-ray radiation in each case with a specifiable x-ray quanta energy distribution, a detector module including at least one x-ray radiation detector for detecting x-ray radiation emitted by the x-ray radiation module, and a computer system. The computer system includes an interface unit that is embodied to capture a first image dataset of the patient representing a first x-ray attenuation distribution of the patient according to a first x-ray quanta energy distribution and at least one second image dataset of the patient representing a second x-ray attenuation distribution of the patient corresponding to a second x-ray quanta energy distribution. The computer system further includes a specification unit that is embodied to specify a virtual x-ray quanta energy distribution. The computer system also includes a calculation unit that is embodied to establish a spatial density distribution in the patient for at least two basic materials, based on the first and the at least one second image dataset, and to create a third image dataset of the patient based on the specifiable, virtual x-ray quanta energy distribution and the established spatial basic material density distributions. The third image dataset represents a third x-ray attenuation distribution of the patient according to the specific, virtual x-ray quanta energy. In addition, the computer system includes a reconstruction unit that is embodied to create the resultant image from the third image dataset.

In accordance with a further aspect, the x-ray imaging device includes an optical sensor that is embodied to capture at least one item of patient-specific, body-related information of the patient. The computer system may further be embodied to cause the optical sensor (e.g., by sending out control signals to the optical sensor) to capture the patient-specific, body-related information of the patient.

In accordance with a further aspect, the x-ray imaging device includes a detector module that includes a spectrally-separating x-ray radiation detector. In this way, the method may be carried out with only one x-ray source with a defined x-ray emission spectrum, and the structure of the x-ray imaging device may be simplified.

DETAILED DESCRIPTION

Figure 1:
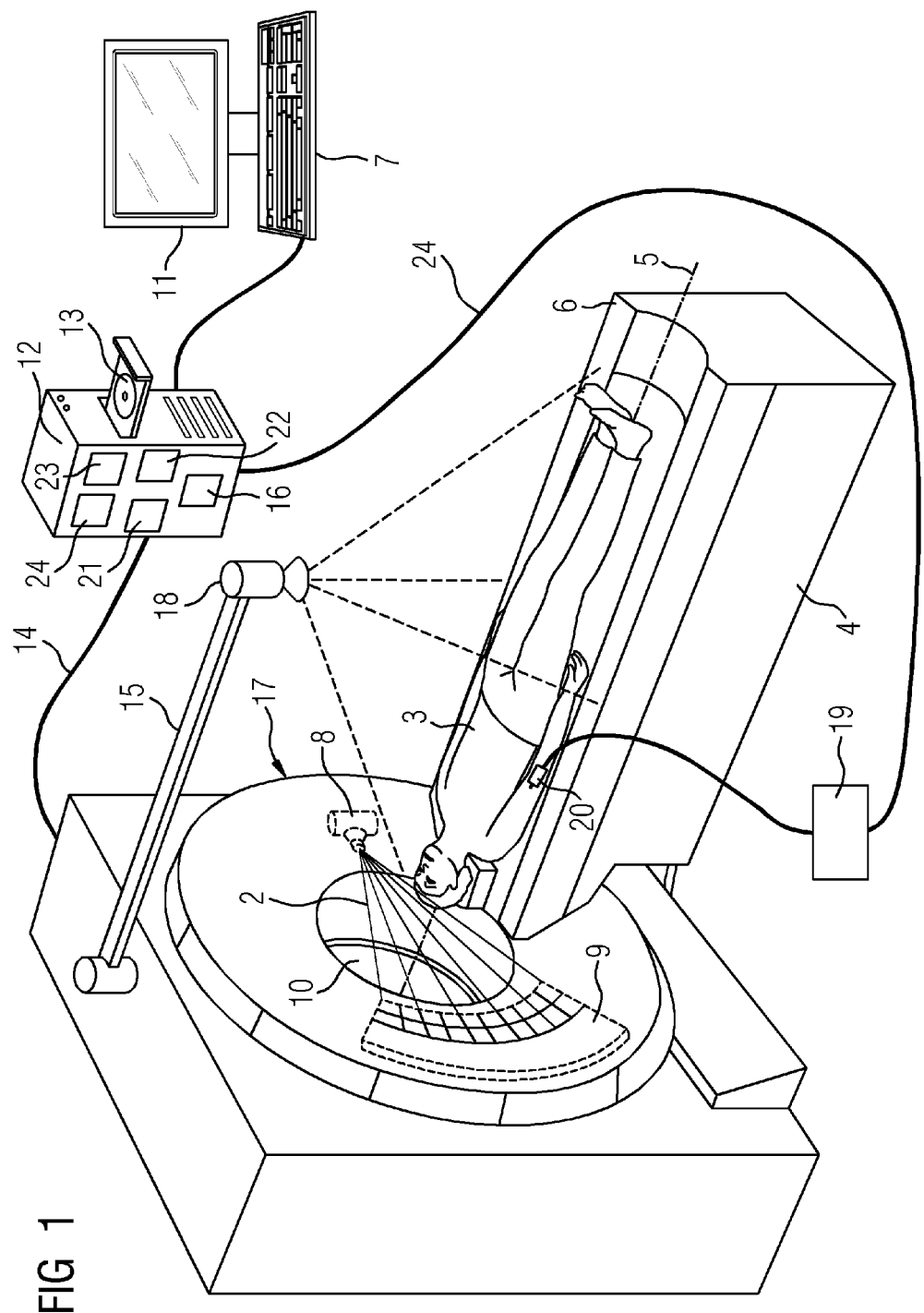
FIG. 1 shows an x-ray imaging device according to an exemplary embodiment.

FIG. 1 shows an x-ray imaging device using an x-ray computed tomograph as an example. The computed tomograph includes, for example, a recording unit 17. The recording unit 17 includes a radiation source 8 in the form of an x-ray source and also a radiation detector 9 in the form of an x-ray detector. The recording unit 17 rotates during the recording of x-ray projections around a system axis 5, and the x-ray source emits rays 2 in the form of x-rays during the recording. The x-ray source involves an x-ray tube. The x-ray detector involves a row detector with a number of rows.

While projections are being recorded, a patient 3 lies on a patient couch 6. The patient couch 6 is connected to a couch pedestal 4 such that pedestal bears the patient couch 6 with the patient 3. The patient couch 6 is configured to move the patient 3 along a direction of recording through the opening 10 of the recording unit 17. The direction of recording is given by the system axis 5, around which the recording unit 17 rotates during the recording of x-ray projections. During a spiral recording, the patient couch 6 is moved continuously through the opening 10 while the recording unit 17 rotates around the patient 3 and records x-ray projections. The x-rays thus describe a spiral on the surface of the patient 3.

The x-ray recording device in this example includes an optical sensor in the form of a camera 18. This is disposed above the patient couch 6 and is connected firmly to the x-ray imaging device via a retaining device 15. The camera 18 may also be fastened to the rotatable recording unit 17. As an alternative, the camera 18 is disposed as a stationary or mobile camera with a free view onto the patient in the examination room (e.g., on the ceiling of the examination room), or the camera 18 is disposed on a mount that is able to be moved freely in the examination room. The camera 18 may be embodied as a two-dimensional camera that creates a two-dimensional representation of an object in grayscales or color values. In this example, the camera 18 is embodied as a three-dimensional camera (e.g., in the form of a stereo camera) time-of-flight camera, or as an interferometric system or the like, and includes the components necessary for the respective recording technology (e.g., suitable light sources and detection units).

The x-ray imaging device further includes a contrast medium administration unit 19. A contrast medium (e.g., in the form of a solution containing iodine) may be administered to the patient 3 via an injection needle 20 during the recording of projections. The flow rate of the contrast medium may be controlled as a function of the time in accordance with a defined injection protocol by the contrast medium administration unit 19. The contrast medium administration unit 19 may be embodied integral with the x-ray imaging device or may be disposed stationary or mobile in the examination room.

The x-ray imaging device includes a computer system 12 in the form of a computer that is connected to a display unit 11 (e.g., for graphic display of reconstructed x-ray images (of resultant images) or to display selection menus relating to the desired virtual x-ray quanta energy distribution), as well as to an input unit 7. The display unit 11 may, for example, involve an LCD, plasma or OLED screen. A touch-sensitive screen may also be involved, which is also embodied as the input unit 7. Such a touch-sensitive screen may be integrated into the imaging device or as part of a mobile device. The input unit 7, for example, involves a keyboard, a mouse, a touch-screen, or also a microphone for voice input. The input unit 7 may also be configured to detect movements of a user and translate the detected movements into corresponding commands. A desired virtual x-ray quanta energy distribution may be selected, for example, by input unit 7.

The computer system 12 is connected to the rotatable recording unit 17 for exchange of information. Via an interface unit 21 and also the connection 14, control signals for the x-ray image recording are transmitted from computer system 12 to the recording unit 17. Different scan protocols, each tuned to an examination type, may be held in a memory 24 and selected by the user before the recording of image data. The recording unit 17 is activated according to the selected scan protocol. Recorded projection data (e.g., in the form of the first and the at least one second image dataset) is captured for further processing in a processing unit 16 (e.g., a processor), described in greater detail below, by the interface unit 21. The connection 14 is realized in the known way as a wired or wireless connection. The computer system 12 is also connected to the camera 18 for exchange of control signals or image data (e.g., via the same connection 14). The computer system 12 is further connected to the contrast medium administration unit 19 for exchange of control signals (e.g., for synchronization of the contrast medium administration with the x-ray image). In the same way, a known wired or wireless connection 24 may be provided.

The computer system 12 also includes a specification unit 22. The computer system 12 is configured, as a function of at least one item of patient-specific (e.g., body-related information for the patient) to provide a specification for the planned examination type and/or as a function of a specification for the desired quality of a resultant image, to specify a virtual x-ray quanta energy distribution. The specification unit 22 may be connected to the display unit 11 and to the input unit 7, in order, for example, to be able to receive and evaluate inputs relating thereto provided by the user or to display possible alternatives to the user for selection. The specification unit 22 may further include a data connection to the processing unit 16 of the computer system 12 in order to be able to use information established by the processing unit 16 relating to patient anatomy, examination type, or desired image quality, and be able to use the information for specifying the virtual x-ray quanta energy distribution. In addition, the specification unit 22 is connected to the processing unit 16 for transmission of the virtual x-ray quanta energy distribution to the processing unit 16. The specification unit 22 may include a part or all of the processing unit 16, the display unit 11, and/or the input unit 7.

The processing unit 16 of the computer system 12 is embodied as an image processing unit or image data processing unit. The processing unit 16 is configured to carry out all computing acts that are related to the method of one or more of the present embodiments on the at least two image datasets and to calculate the third image dataset. For example, the processing unit is embodied to carry out a material decomposition with reference to the at least two image datasets. The processing unit is further embodied to establish at least one item of patient-specific, body-related information for the patient 3 from topogram data, x-ray images, or from data captured by optical sensor 18. The processing unit is further embodied to derive an examination type from specifications for a scan protocol used for recording image data.

The processing unit 16 may interact with a computer-readable data medium 13 (e.g., in order to carry out a method by a computer program with program code). The computer program may be stored retrievably on the machine-readable medium (e.g., a non-transitory computer-readable storage medium). For example, the machine-readable medium may involve a CD, DVD, Blu-Ray disk, a memory stick or a hard disk. The processing unit 16 may be embodied in the form of hardware or in the form of software. For example, the processing unit 16 is embodied as a Field Programmable Gate Array (FPGA) or includes an arithmetic logic unit.

In the example shown, at least one computer program is stored in the memory 24 of the computer system 12, which carries out all method acts of the method when the computer program is executed on the computer. The computer program for executing the method acts of the method includes program code. The computer program may be embodied as an executable file and/or be stored on a processing system other than the computer system 12. For example, the x-ray imaging device may be configured so that the computer system 12 loads the computer program for carrying out the method into an internal main memory via an intranet or via the Internet.

The memory 24 of the computer system 12 is further embodied to store energy-dependent x-ray attenuation values for a plurality of basic materials. The values are stored in the form of tables, for example. For example, x-ray attenuation values are stored for each basic material for different x-ray quanta energies. X-ray attenuation values for x-ray quanta energies not included may be obtained, for example, by the processing unit 16 through known interpolation methods. The memory 24 of the computer system 12 is further embodied to store topogram data, x-ray images of earlier x-ray examinations, data of the patient 3 to be imaged captured by optical sensor 18, or the like, and provide the data to the processing unit 16 possibly for an evaluation. Processing unit 16 and memory 24 are accordingly connected for exchange of data. As an alternative, the computer system 12 is connected to a Radiological Information system (RIS) network or to a Picture Archiving and Communication System (PACS) network for retrieval of the information or data, which may be stored in the RIS or PACS network.

Processing unit 16 and output unit 11 or input unit 7 also have a data connection in order, for example, to display to the user a selection menu relating to the desired basic materials or to be able to receive specifications from the user relating thereto. Processing unit 16 and output unit 11 or input unit 7 may also be connected via the specification unit 22 for transmission of the specifiable, virtual x-ray quanta energy distribution.

In addition, the computer system 12 also includes a reconstruction unit 23 that is configured, in accordance with known reconstruction methods, to calculate a resultant image for the specifiable, virtual x-ray quanta energy distribution from the third image dataset. There is a data connection between display unit 11 and reconstruction unit 23 for transmission and display of resultant images.

Figure 2:
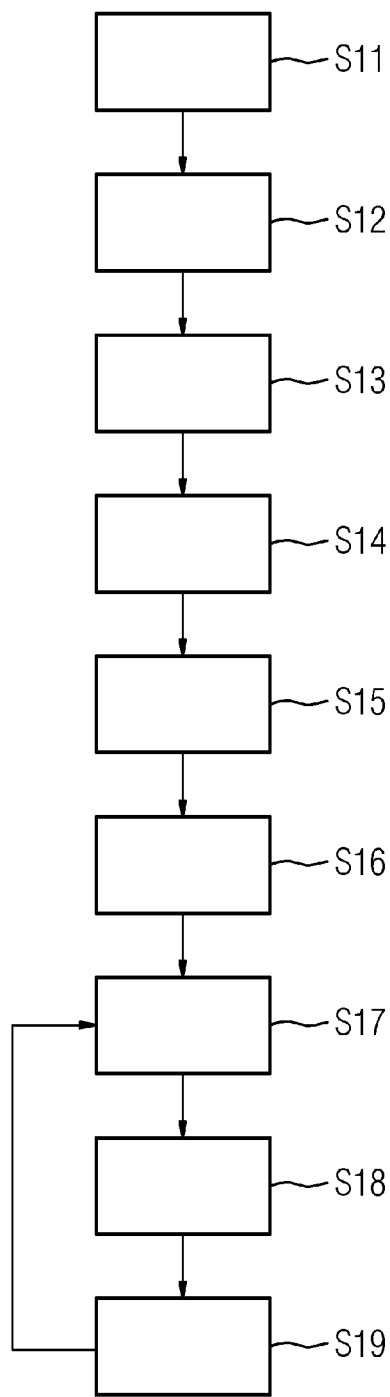
FIG. 2 shows a flow diagram of a method according to a first exemplary embodiment.

FIG. 2 describes a first exemplary embodiment of a method. According to this example, the recording of one or more x-ray images with an acceleration voltage set in accordance with a desired image impression is replaced by the computation or simulation of a resultant image for a virtual x-ray quanta energy distribution from image datasets recorded with other acceleration voltages. The virtual x-ray quanta energy distribution approximates the average energy of the emission spectrum for the set or actually desired acceleration voltage, or corresponds to the voltage. In other words, a resultant image that gives an image impression that is comparable to the one x-ray image that would actually have been recorded with the acceleration voltage corresponding to the desired image impression is created in this way. The exemplary embodiment looks at the retrospective specification of the virtual x-ray quanta energy distribution.

The resultant image is computed from two image datasets corresponding to x-ray quanta energy distributions differing from one another, based on a two-material decomposition. The method described is, however, readily able to be transferred to the computation of the image from more than two image datasets based on a multi-material decomposition.

In act S11, a first dataset and a second image dataset of the patient 3 are captured from the recording unit 17 via the interface unit 21 by the computer system 12 and transmitted to the processing unit 16. The capturing of the image datasets may also include the recording of the projection data with the recording unit 17. The two image datasets have been recorded with a dual-source x-ray imaging device with acceleration voltages of 80 kV and 140 kV. Thereafter, in act S12, the basic materials in which a subsequent material decomposition is to take place are determined. The processing unit 16 may evaluate the scan protocol underlying the image dataset recording and, as a function of the examination type defined therein, may define two basic materials. As an alternative, the processing unit may analyze the captured image datasets with respect to the region of the body of the patient imaged and derive two suitable basic materials therefrom. There is the further option that the processing unit 16 displays to the user via the display unit 11 a choice of possible materials for selection and that the user defines the basic materials by clicking with the mouse on the display unit 11, for example. In the present example, the materials iodine and soft tissue are considered. In act S13, in a known way, the basic material decomposition is undertaken based on the x-ray attenuation distribution of the patient 3 able to be taken from the first image dataset and the second image dataset in the imaged region of the body to iodine and soft tissue for determining the density distributions or the material proportions of the material in the imaged body region. The virtual x-ray quanta energy distribution is specified based on an analysis of the individual patient anatomy. To do this, the optical sensor 18, in act S14, captures the three-dimensional body surface of the patient 3 and translates this in act S15 into a three-dimensional surface model. For example, the surface model describes the surface contour formed by the skin in slices along the body axis of the patient 3. The processing unit 16 also establishes the weight of the patient 3 in act S15 based on the surface model. To do this, the surface model is supplemented with respect to the missing, non-scanned regions of the surface of the patient. In this example, the rear side of the patient is missing in order to obtain a complete (e.g., closed) three-dimensional surface model and thus the patient volume. This is done with known extrapolation methods or with the assistance of a three-dimensional model of the patient couch, which is fitted by the processing unit 16 into the surface model. Assuming a density for the patient's body, the patient's weight is produced. In a further act S16, the processing unit determines, by evaluating the above-mentioned scan protocol, the planned examination type. An angiography recording may be created while administering a contrast medium containing iodine, for which the contrast-to-noise ratio is important. In act S17, the virtual x-ray quanta energy distribution is specified. In this example, this corresponds to a discrete x-ray quanta energy value. The specification unit 22 evaluates the previously-determined patient-specific, body-related information (e.g., body surface and patient weight), as well as the examination type and derives a value for the virtual x-ray quanta energy distribution that best takes account of the variables with respect to the quality or expressiveness of the resultant image to be achieved. As an alternative, the virtual x-ray quanta energy distribution is specified by a user while excluding acts S14 to S15. The user is presented by the specification unit 22 via the display unit 11 with a sliding control that may be adjusted on a bar representing different values for the specifiable, virtual x-ray quanta energy distribution by input unit 7. Thus, the left-hand end of the bar may represent a smallest-possible x-ray quanta energy value of 40 keV, while the right-hand end of the bar represents a largest-possible x-ray quanta energy value of 110 keV. By moving the control using input unit 7, for example, via activation of the control by clicking on the control with the mouse and moving the control by moving the mouse along the bar, the user may select what the user sees as an optimum virtual x-ray quanta energy distribution, which lies between 40 keV and 110 keV. In both alternatives, the virtual x-ray quanta energy distribution is determined to be 50 keV, which corresponds to an average value of the x-ray quanta energy values of an emission spectrum for an acceleration voltage of 80 kV. This value is transmitted by the specification unit 22 to the processing unit 16, so that the unit may create a third image dataset in act S18 based on the computed material portions of the basic materials for the virtual x-ray quanta energy distribution. To do this, the processing unit 16 accesses tables stored in local memory 24 or in an RIS or PACS network for iodine and soft tissue, from which the processing unit 16 takes the respective x-ray attenuation values for the virtual x-ray quanta energy. These x-ray attenuation values will subsequently be added weighted according to the material proportions. From the third image dataset, the reconstruction unit 23 reconstructs the resultant image in act S19. The resultant image may be output directly to the user via the display unit 11 for appraisal. If the user establishes that the specification of the virtual x-ray quanta energy distribution by the user or by the processing unit is unsatisfactory or is not yet optimum, the user may enter another value for the virtual x-ray quanta energy distribution by displaying the slider control described above again, for which a further resultant image in accordance with method acts S17 to S19 may be created. In this way, the user may continuously adapt the image impression of the resultant image to the image impression desired by the user (e.g., with respect to an optimum contrast-to-noise ratio). The sequence of acts S12 to S16 of the method in accordance with this example is not fixed, as described above, but may be altered in any way.

Figure 3:
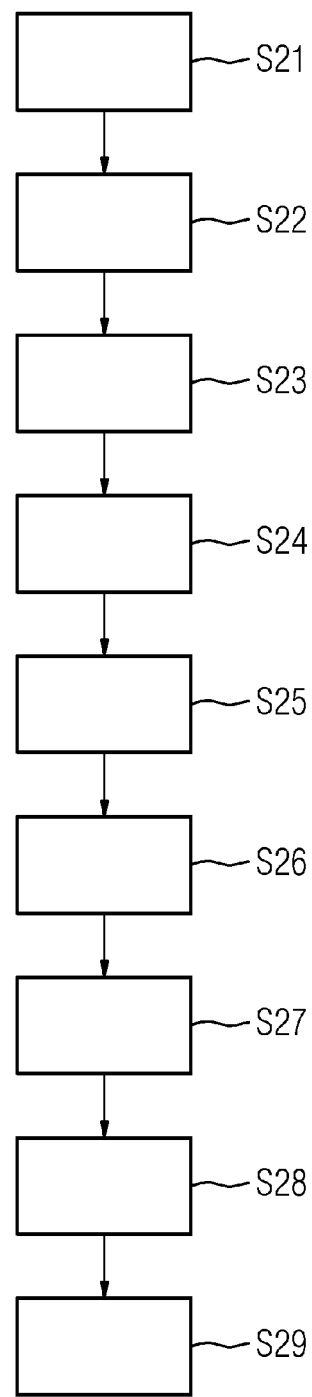
FIG. 3 shows a flow diagram of a method according to a further exemplary embodiment.

FIG. 3 describes a second exemplary embodiment of the method. In this example, a resultant image is created. The resultant image gives an image impression that is comparable to that of an x-ray image that would actually have been recorded with the acceleration voltage corresponding to a desired image impression. This example looks at a prospective specification of the virtual x-ray quanta energy distribution. The resultant image is computed from two image datasets and may be produced from a multi-material decomposition. The specification of the virtual x-ray quanta energy distribution is based on an analysis of the planned examination type as well as an analysis of the required image quality of the resultant image.

In act S21, the planned examination type is established. The user may select the planned type from a plurality of examination types via the display unit 11 and input unit 7. As an alternative, the processing unit 16 evaluates the scan protocol set for image data recording and in this way, obtains information for the planned examination type. In act S22, the necessary image quality of the resultant image is defined. This varies mainly with the planned examination type. Thus, for example, in an examination of the abdomen, a high contrast-to-noise ratio is decisive for the meaningfullness of the resultant image (e.g., indicative of the specification of a smaller x-ray quanta energy distribution). In addition, the image quality also takes account of artifacts. For example, the virtual x-ray quanta energy distribution may be specified so that metal artifacts will largely be suppressed (e.g., indicative of the specification of a higher). In the individual case, a compromise between the two is to be found. While taking account of the information, the specification unit 22, in act S23, specifies an optimum, virtual x-ray quanta energy distribution. To do this, the specification unit 22 initially specifies the emission spectrum of the acceleration voltage that would be used for the recording of an image dataset in order to fulfill the requirements as regards examination type and image quality. Emission spectra for different acceleration voltages may be held in the memory 24 or in an RIS or PACS network for retrieval by the specification unit 22. The virtual x-ray quanta energy distribution is composed of a plurality of discrete x-ray quanta energy values within the identified emission spectrum in this example. As an alternative, a number of acceleration voltages are displayed to the user in act S23 by the specification unit 22 via the display unit 11, which the user may select via the input unit 7 in accordance with the conventional method of operation. In this way, the user is given the impression of a familiar process sequence for image data recording. For the selected acceleration voltage, the specification unit 22 establishes an emission spectrum as described and derives the x-ray quanta energy distribution from a number of discrete x-ray quanta energy values within the emission spectrum. In an optional act S24, the current of the one or more x-ray sources is adapted in accordance with the selected acceleration voltage, the planned examination type, and/or the anatomy of the patient. In this way, the dose applied to the patient 3 during image data recording may be reduced. Act S25 corresponds to the capture of two image datasets with an x-ray quanta energy distribution that differs and that deviates from the specifiable, virtual x-ray quanta energy distributions, which may also include the image data recording. These x-ray quanta energy distributions are specified or determined, for example, via a spectral filter used with an x-ray source. The acts S26 to S29 include the selection of two basic materials, the computation of the density distributions and material proportions of the basic materials in the patient, the creation of a third image dataset for the specifiable, virtual x-ray quanta energy distribution, and the reconstruction of the resultant image from the third image dataset. In this case, the third image dataset is formed as an average value from the computed, effective x-ray attenuation values for the discrete x-ray quanta energy values. In relation to the remaining acts, please reference the disclosure relating to FIG. 2.

Individual acts or individual aspects of the two examples of the method are able to be interchanged with one another.

The described acts for basic material decomposition and for creating the at least one third image dataset may be carried out, in a way known to the person skilled in the art, both in the image space and also in the projection space. Both methods of operation are of equal value with respect to the method. However, the computing acts may be carried out significantly more easily in the image space, since a computation may be performed picture element by picture element.

The created resultant image may be subjected to a known method for enhancing the image quality retrospectively or during reconstruction. For example, the image noise of a resultant image may be reduced in order to align the image quality of the resultant image to that of a classical and comparable x-ray image recorded by a corresponding acceleration voltage.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for creating a resultant image of a patient with an x-ray imaging device for a specifiable, virtual x-ray quanta energy distribution, the method comprising:
    capturing a first image dataset of the patient, the first image dataset representing a first x-ray attenuation distribution of the patient in accordance with a first x-ray quanta energy distribution;
    capturing at least one second image dataset of the patient, the at least one second image dataset representing at least one second x-ray attenuation distribution of the patient corresponding to at least one second x-ray quanta energy distribution;
    specifying a virtual x-ray quanta energy distribution as a function of a predetermined clinical issue;
    establishing a spatial density distribution of the patient for at least two materials based on the first image dataset and the at least one second image dataset;
    creating a third image dataset of the patient based on the specified virtual x-ray quanta energy distribution and the established spatial material density distributions, wherein the third image dataset represents a third x-ray attenuation distribution of the patient corresponding to the specified virtual x-ray quanta energy distribution; and
    creating the resultant image from the third image dataset.

2. The method of claim 1, wherein the first image dataset and the at least one second image dataset are captured with a spectrally-separating x-ray radiation detector.

3. The method of claim 2, wherein the first image dataset and the at least one second image dataset are captured with a quanta-counting detector or a dual-layer detector.

4. The method of claim 1, wherein specifying the virtual x-ray quanta energy distribution as a function of a predetermined clinical issue comprises specifying the virtual x-ray quanta distribution as a function of desired image quality.

5. The method of claim 4, wherein the virtual x-ray quanta energy distribution is specified as a function of desired image quality with respect to an improved contrast-to-noise ratio, reduced image noise, or reduced artifacts.

6. The method of claim 1, wherein the virtual x-ray quanta energy distribution is specified after the capturing of the first image dataset and the at least one second image dataset with an x-ray imaging device.

7. The method of claim 1, wherein the virtual x-ray quanta energy distribution is specified by a user.

8. The method of claim 1, wherein the at least two materials comprise iodine and soft tissue.

9. A method for creating a resultant image of a patient with an x-ray imaging device for a specifiable, virtual x-ray quanta energy distribution, the method comprising:
    capturing a first image dataset of the patient, the first image dataset representing a first x-ray attenuation distribution of the patient in accordance with a first x-ray quanta energy distribution;
    capturing at least one second image dataset of the patient, the at least one second image dataset representing at least one second x-ray attenuation distribution of the patient corresponding to at least one second x-ray quanta energy distribution;
    specifying a virtual x-ray quanta energy distribution;
    establishing a spatial density distribution of the patient for at least two materials based on the first image dataset and the at least one second image dataset;
    creating a third image dataset of the patient based on the specified virtual x-ray quanta energy distribution and the established spatial material density distributions, wherein the third image dataset represents a third x-ray attenuation distribution of the patient corresponding to the specified virtual x-ray quanta energy distribution; and
    creating the resultant image from the third image dataset, wherein specifying the virtual x-ray quanta energy distribution comprises specifying the virtual x-ray quanta energy distribution as a function of at least one item of patient-specific, body-related information of the patient.

10. The method of claim 9, wherein the at least one item of patient-specific, body-related information comprises patient height, patient width, patient shape, patient weight, x-ray attenuation behavior of the patient, or any combination thereof.

11. The method of claim 9, further comprising capturing, by an optical sensor, the at least one item of patient-specific, body-related information of the patient.

12. The method of claim 11, wherein the optical sensor comprises a three-dimensional camera.

13. The method of claim 1, wherein specifying the virtual x-ray quanta energy distribution as a function of a predetermined clinical issue comprises specifying the virtual x-ray quanta distribution as a function of an examination type.

14. In a non-transitory computer-readable storage medium that stores instructions executable by a computer to create a resultant image of a patient with an x-ray imaging device for a specifiable, virtual x-ray quanta energy distribution, the instructions comprising:
    capturing a first image dataset of the patient, the first image dataset representing a first x-ray attenuation distribution of the patient in accordance with a first x-ray quanta energy distribution;
    capturing at least one second image dataset of the patient, the at least one second image dataset representing at least one second x-ray attenuation distribution of the patient corresponding to at least one second x-ray quanta energy distribution;
    specifying a virtual x-ray quanta energy distribution as a function of a predetermined clinical issue or at least one item of patient-specific, body-related information of the patient;
    establishing a spatial density distribution of the patient for at least two materials based on the first image dataset and the at least one second image dataset;
    creating a third image dataset of the patient based on the specified virtual x-ray quanta energy distribution and the established spatial material density distributions, wherein the third image dataset represents a third x-ray attenuation distribution of the patient corresponding to the specified virtual x-ray quanta energy distribution; and
    creating the resultant image from the third image dataset.

15. The method of claim 14, wherein specifying the virtual x-ray quanta energy distribution as a function of a predetermined clinical issue comprises specifying the virtual x-ray quanta distribution as a function of an examination type.

16. The method of claim 14, wherein specifying the virtual x-ray quanta energy distribution as a function of a predetermined clinical issue comprises specifying the virtual x-ray quanta distribution as a function of desired image quality.

17. An x-ray imaging device for creating a resultant image of a patient for a specifiable, virtual x-ray quanta energy distribution, the x-ray imaging device comprising:
    an x-ray module comprising at least one x-ray source, each x-ray source of the at least on x-ray source being operable to create and emit x-ray radiation with a specified x-ray quanta energy distribution;
    a detector module comprising at least one x-ray radiation detector, each x-ray radiation detector of the at least one x-ray radiation detector being operable to detect x-ray radiation emitted by the x-ray module; and
    a computer system configured to:
        capture a first image dataset of the patient, the first image dataset representing a first x-ray attenuation distribution of the patient in accordance with a first x-ray quanta energy distribution;
        capture at least one second image dataset of the patient, the at least one second image dataset representing at least one second x-ray attenuation distribution of the patient corresponding to at least one second x-ray quanta energy distribution;
        specify a virtual x-ray quanta energy distribution as a function of a predetermined clinical issue or at least one item of patient-specific, body-related information of the patient;
        establish a spatial density distribution of the patient for at least two materials based on the first image dataset and the at least one second image dataset;
        create a third image dataset of the patient based on the specified virtual x-ray quanta energy distribution and the established spatial material density distributions, wherein the third image dataset represents a third x-ray attenuation distribution of the patient corresponding to the specified virtual x-ray quanta energy distribution; and
        create the resultant image from the third image dataset.

18. The x-ray imaging device of claim 17, wherein the computer system comprises:
    an interface unit configured to capture the first image dataset of the patient and the at least one second image dataset of the patient;
    a specification unit configured to specify the virtual x-ray quanta energy distribution;
    a processor configured to:
        establish the spatial density distribution in the patient for the at least two materials based on the first image dataset and the at least one second image dataset; and
        create a third image dataset of the patient based on the specified virtual x-ray quanta energy distribution and the established spatial material density distributions; and
    a reconstruction unit configured to create the resultant image from the third image dataset.

19. The x-ray imaging device of claim 17, further comprising an optical sensor configured to capture at least one item of patient-specific, body-related information of the patient.

20. The x-ray imaging device of claim 17, wherein the detector module comprises a spectrally-separating x-ray radiation detector.

21. The method of claim 17, wherein specifying the virtual x-ray quanta energy distribution as a function of a predetermined clinical issue comprises specifying the virtual x-ray quanta distribution as a function of an examination type.

22. The method of claim 17, wherein specifying the virtual x-ray quanta energy distribution as a function of a predetermined clinical issue comprises specifying the virtual x-ray quanta distribution as a function of desired image quality.

* * * * *